United States Patent [19]

Hooven

[11] Patent Number: 4,714,458
[45] Date of Patent: Dec. 22, 1987

[54] THREE STAGE VALVE WITH FLEXIBLE VALVE SEAT

[75] Inventor: Michael D. Hooven, Miami, Fla.

[73] Assignee: Cordis Corporation, Miami, Fla.

[21] Appl. No.: 812,771

[22] Filed: Dec. 23, 1985

[51] Int. Cl.[4] .......................................... A61M 27/00
[52] U.S. Cl. ...................................... 604/9; 137/504; 137/508; 604/247
[58] Field of Search ............... 137/504, 508, 539, 859; 138/45; 604/8–10, 247

[56] References Cited

U.S. PATENT DOCUMENTS

| 28,722 | 6/1860 | Whitacher | 137/508 |
|---|---|---|---|
| 79,436 | 6/1868 | Bechtel | 137/508 |
| 1,139,455 | 5/1915 | Gase | 137/508 |
| 1,159,214 | 11/1915 | Gueux | 137/508 |
| 1,199,152 | 9/1916 | Bruce | 137/508 |
| 1,468,434 | 9/1923 | Zander | |
| 2,207,382 | 7/1940 | McNamara | 277/21 |
| 2,290,151 | 7/1942 | McCollum | 237/12.3 |
| 2,684,081 | 7/1954 | Chace | 137/517 |
| 2,960,109 | 11/1960 | Wilson | 137/859 X |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 128/350 |
| 3,308,798 | 3/1967 | Snider | 123/119 |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,693,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Steuby | 137/496 |
| 3,804,113 | 4/1974 | Garcea | 137/496 |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton et al. | 137/498 |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,103,689 | 8/1978 | Leighton | 128/350 V |
| 4,106,510 | 8/1978 | Hakim et al. | 128/350 V |
| 4,156,422 | 5/1979 | Hildebrandt et al. | 128/748 |
| 4,167,952 | 9/1979 | Reiniecke | 137/493 |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,437,493 | 3/1984 | Okuda et al. | 138/45 |
| 4,443,214 | 4/1984 | Marion | 604/9 |
| 4,451,128 | 11/1985 | Hakim et al. | 604/9 |
| 4,452,423 | 6/1984 | Bevlavi | 251/65 |
| 4,627,832 | 12/1986 | Hooven et al. | 604/9 |

FOREIGN PATENT DOCUMENTS 68509 8/1951 Netherlands.

Primary Examiner—Dalton L. Truluck
Attorney, Agent, or Firm—Lockwood, Alex, FitzGibbon & Cummings

[57] ABSTRACT

An implantable valve for controlling the passage of cerebrospinal fluid (CSF) from a ventricle of the brain to a suitable drainage location in the body includes a movable diaphragm, one side of which is in pressure communication with the drainage location of the body and the other side of which is in pressure communication with the ventricular spaces of the brain. The diaphragm includes a flexible valve seat which moves relative to a valve closure means and a fluid flow control means in response to applied pressure differentials, thus regulating passage of CSF from the ventricular spaces to the drainage location. When the pressure differential is relatively small, the valve operates in a constant pressure mode to maintain a predetermined pressure differential across the valve. In response to a sudden increase in differential pressure, the valve operates in a constant flow mode to maintain a desired relatively constant CSF flow rate through the valve. Above a predetermined pressure differential, the valve operates n a constant pressure mode to maintain a predetermined maximum pressure differential across the valve.

7 Claims, 10 Drawing Figures

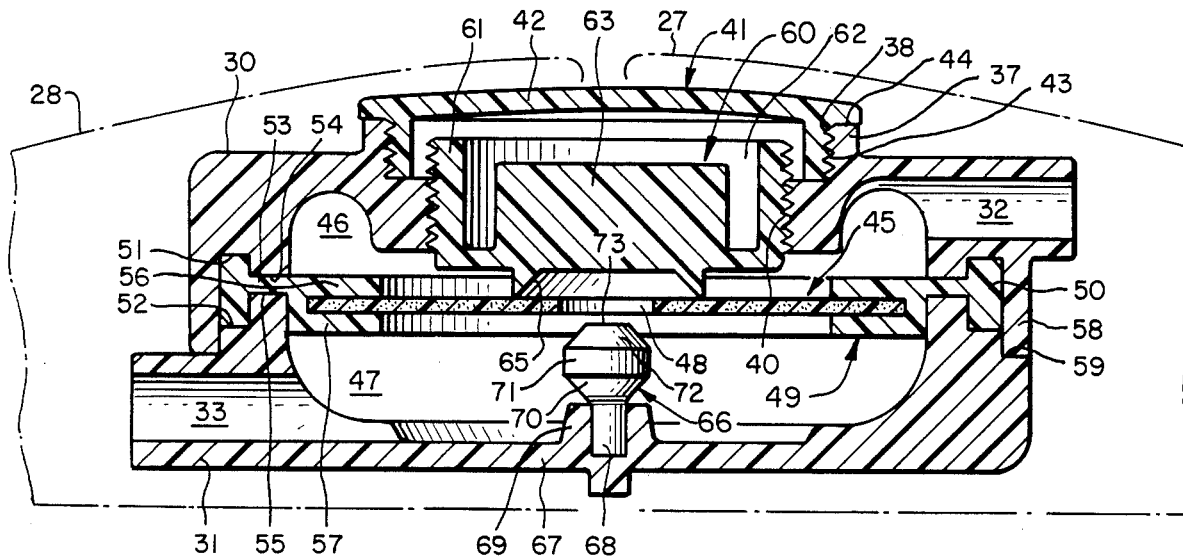
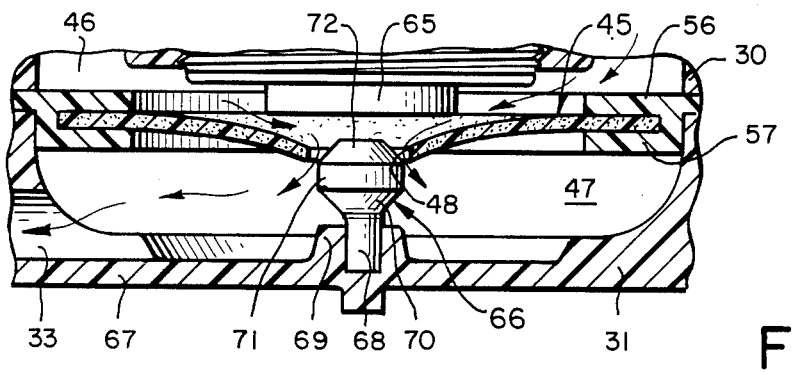
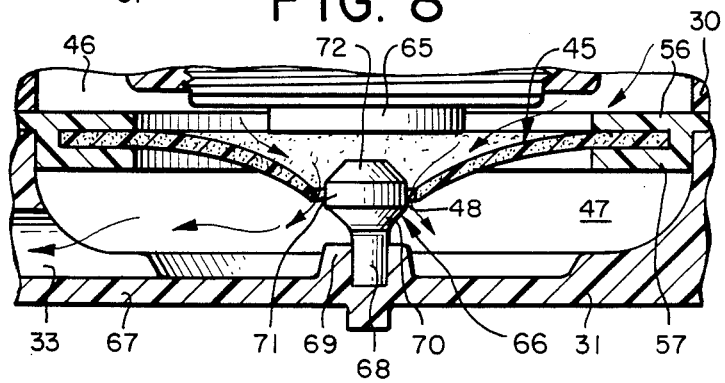
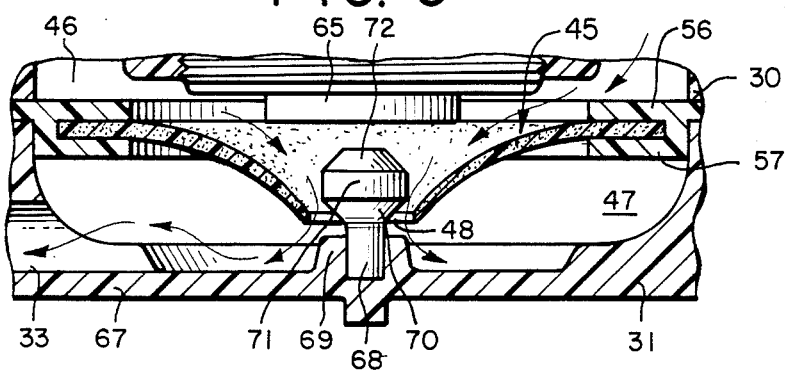

THREE STAGE VALVE WITH FLEXIBLE VALVE SEAT

BACKGROUND OF THE INVENTION

The present invention relates to an intracranial pressure relief valve including a flexible valve seat portion which cooperates with a valve closure member and a fluid flow control member for three stage operation of the type which provides either constant pressure or constant flow characteristics in response to a fluid pressure differential applied across the valve.

Hydrocephalus is a condition in which the body, for any one of a variety of reasons, is unable to relieve itself of excess cerebrospinal fluid (CSF) collected in the ventricles of the brain. The excessive collection of CSF in the ventricles results in an abnormal increase in both epidural and intradural pressures. This in turn causes a number of adverse physiological effects including compression of brain tissue, impairment of blood flow in the brain tissue and impairment of the brain's normal metabolism.

Treatment of a hydrocephalic condition frequently involves relieving the abnormally high intracranial pressure. To this end, a variety of CSF pressure regulator valves and methods of controlling CSF pressure have been developed which include various check valves, servo valves and combinations thereof. Generally, such valves serve to divert CSF from the ventricles of the brain through a discharge line to some suitable drainage location in the body, such as the venous system or the peritoneal cavity. Check valves operate by opening when the difference between CSF pressure and pressure in the discharge line exceeds a predetermined value.

The use of a simple check valve in the treatment of hydrocephalus is potentially disadvantageous since it is possible for such a valve to open in response to a sudden, but nevertheless perfectly normal, increase in differential pressure between CSF in the ventricular spaces and fluid at the selected discharge location of the body, resulting in abnormal and potentially dangerous hyperdrainage of the ventricular spaces. For example, when a patient stands after lying in a recumbent position, the resulting increased vertical height of the fluid column existing between the head and the selected drainage location may result in such an increase in differential pressure. Accordingly, valves, such as that described in the copending application of the present inventor, Ser. No. 672,868, filed Nov. 19, 1984, have been developed which serve to prevent undesired hyperdrainage by limiting the flow rate of fluid through the valve when a sudden increase in differential pressure occurs.

In this valve, the diaphragm, movable in response to the pressure differential between ventricular CSF pressure and pressure of fluids at the drainage location of the body, was mechanically coupled to a rigid valve seat having a fluid metering orifice extending therethrough. The orifice allowed passage of CSF from the ventricular spaces to the selected drainage location. Motion of the diaphragm in response to changes in the differential pressure caused the valve seat to be moved from a first position, in which the valve seat contacted a suitably located sphere to block and thereby prevent the passage of fluid through the orifice, to a second position, in which a generally cylindrical fluid flow restrictor partially occluded the orifice, thereby limiting fluid flow therethrough. By controlling the position of the sphere, the valve seat and the restrictor, it was possible to construct a valve having flow characteristics which avoided hyperdrainage with sudden changes in differential pressure.

Needless to say, in miniaturized valves of the type under consideration, it is necessary to carefully control the dimensions of the various components of the valve. Since the parts involved are quite small, necessitating working tolerances on the order of 0.0001 of an inch, considerable manufacturing costs can be incurred in constructing such a valve.

The present invention is directed to an improvement in such a valve wherein the parts thereof are designed to hold manufacturing costs at minimum as well as simplify the manufacturing steps involved. More particularly, by reason of certain features of the valve of the present invention, greater flexibility in utilization of the valve is available. Basically, a valve constructed in accordance with the present invention is provided with a flexible valve seat which forms a part of the movable diaphragm and which defines the fluid flow orifice. The dimensions and degree of flexibility of the valve seat can be readily varied through relatively uncomplicated molding techniques. The remainder of the valve involves the use of a readily manufactured form of valve closure member as well as an uncomplicated and readily manufactured fluid flow control member, these elements cooperating with the flexible seat to provide the much desired three stage operation.

In view of the foregoing, it is a general object of the present invention to provide a new and improved pressure regulator valve for relieving intracranial pressure caused by the presence of excess CSF in the ventricles of the brain.

It is a more specific object of the present invention to provide a pressure regulator valve which includes components which may be economically manufactured.

It is a still more specific object of the present invention to provide a pressure regulator valve in which critically dimensioned components are of a readily manufactured configuration.

SUMMARY OF THE INVENTION

The invention is directed to a valve for controlling the passage of body fluids from one location in the body to another location. The valve includes a housing having first and second interior chambers. An inlet port establishes fluid communication between the first chamber and the one location, while an outlet port establishes fluid communication between the second chamber and the other location. The valve mechanism of the invention includes a flexible diaphragm which is provided with a flexible and stretchable valve seat portion defining a fluid flow orifice by means of which fluid is transferred from the first chamber into the second chamber. A valve seat closure member cooperates with the flexible seat to establish a first condition in which fluid communication between the first and second chambers is prevented. A fluid flow control member is aligned with the orifice of the flexible seat and cooperative functioning therebetween results in operation of the valve in response to changes in differential pressure to a second condition in which fluid communication is provided between the first and second chambers at a flow rate sufficient to maintain a substantially constant desired first pressure in the first chamber, to a third condition in which fluid communication is provided between the first and second chambers sufficient to maintain a desired substantially constant fluid flow rate, and to a fourth condition in which fluid communication is provided between the first and second chambers sufficient to maintain a substantially constant desired second pressure in the first chamber. In this manner the valve mechanism sequentially prevents the passage of fluid between the one location and the other location, maintains a constant fluid pressure differential between the one location and the other location, maintains a desired constant rate of flow of fluid between the one location and the other location, and maintains a second constant desired fluid pressure differential between the one location and the other location.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 6 is an enlarged cross-sectional view of the pressure regulator valve taken along line 6—6 of FIG. 5.

FIG. 7 is a cross-sectional view, similar to FIG. 6, showing the pressure regulator valve in a first constant pressure mode.

FIG. 8 is a cross-sectional view, similar to FIG. 6, showing the pressure regulator valve in a constant flow-rate mode.

FIG. 9 is a cross-sectional view, similar to FIG. 6, showing the pressure regulator valve in a second constant pressure mode.

DESCRIPTION OF THE PREFERRED EMBODIMENT

Figure 1:
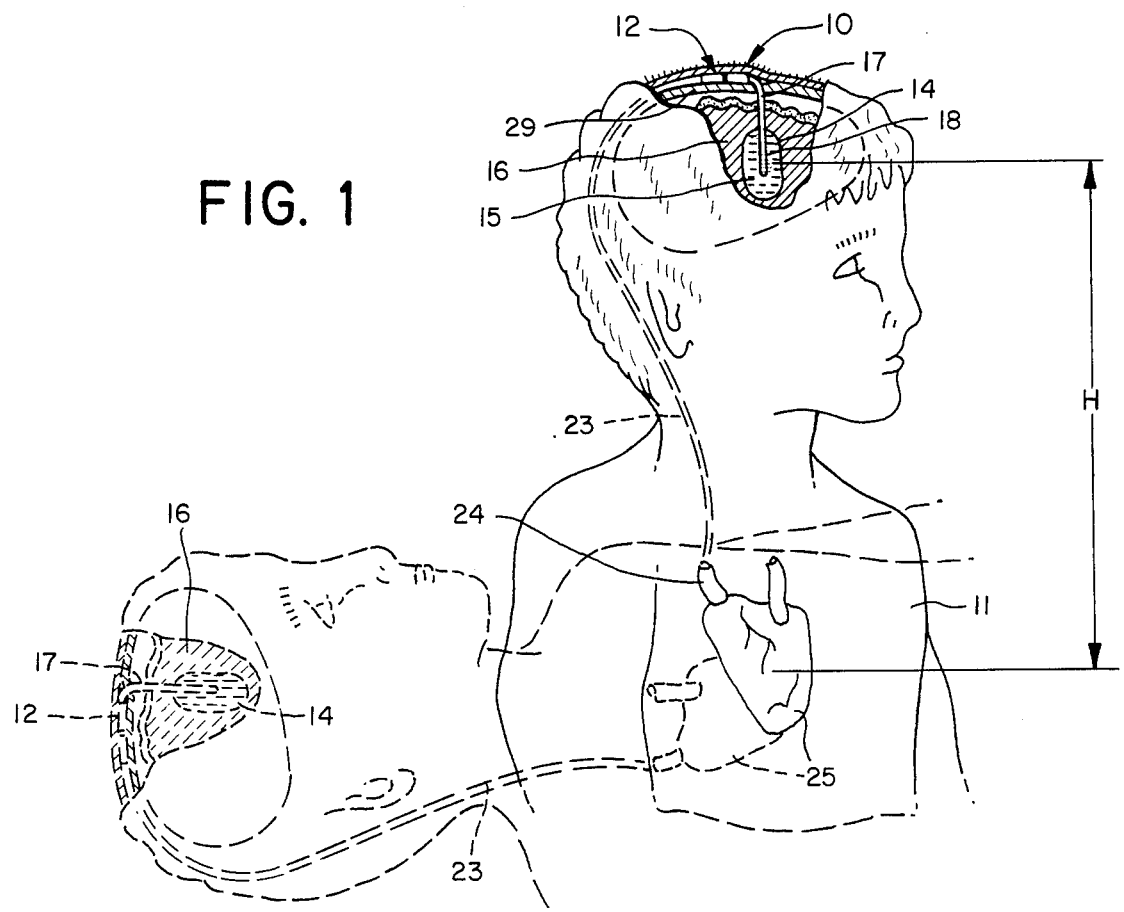
FIG. 1 is a perspective view, partially in section, of a CSF pressure relief system employing a three stage pressure regulator valve having a flexible valve seat member constructed in accordance with the invention, showing such a system implanted within a patient.
Figure 2:
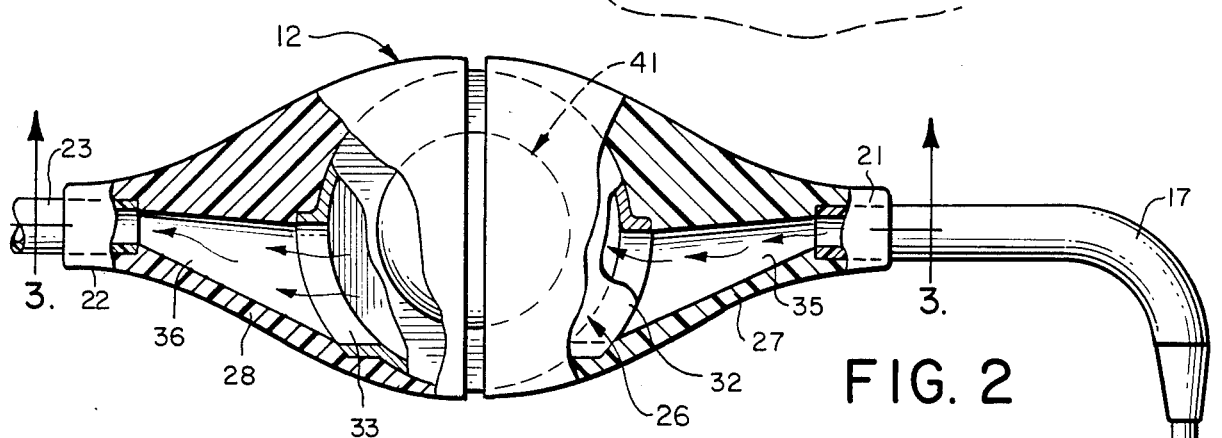
FIG. 2 is a plan view, partially in section, of the pressure regulator valve showing the principal elements thereof.
Figure 3:
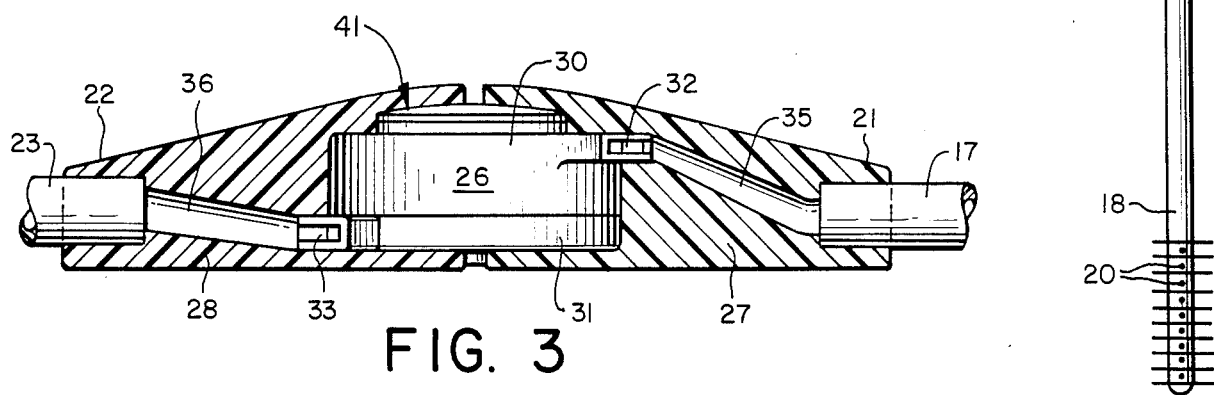
FIG. 3 is a cross-sectional view of the pressure regulator valve taken along line 3—3 of FIG. 2.

Referring to the drawings, and particularly to FIGS. 1-3, a CSF pressure relief system 10 for maintaining a desired predetermined intracranial pressure in a patient 11 is illustrated. The system shown includes a three stage pressure relief valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement with the brain. The distal end 18 of the catheter may be provided with a plurality of apertures 20 (FIG. 2) for allowing the passage of CSF therethrough and is positioned in a suitable brain ventricle as illustrated. The other end of the catheter is coupled to the inlet port 21 of the valve to establish fluid communication between the valve and the ventricle. The outlet port 22 of the valve is attached to one end of a drain catheter 23, the opposite end of which discharges into an appropriate location in the patient's body. Although the drain catheter is shown threaded through an appropriate vein 24 to terminate within the right atrium of the heart 25, a different drainage location, such as, for example, the peritoneal cavity, could be selected instead. When open, pressure relief valve 12 allows passage of CSF from the brain ventricle to the selected discharge location to relieve excessive intracranial pressure caused by excessive accumulation of CSF. Typically, pressure relief valve 12 includes means for adjusting the differential pressure threshold at which it opens so that the hydrocephalus pressure relief system can be adjusted to suit the specific requirements of an individual patient.

While an increased differential pressure may result from the excessive accumulation of CSF in the brain ventricle, such an increase might also be a perfectly normal response to ordinary physical activity of the patient. For example, when a patient stands after lying for some time in a recumbent position, as illustrated in phantom in FIG. 1, the differential pressure will suddenly increase by reason of the sudden increase in vertical height H of the fluid column existing between the distal end of the ventricular catheter and the drainage location. If the relief valve were to open and permit unrestrained fluid flow in response to this pressure increase, hyperdrainage of the ventricle, and a brain hematoma, are possible results. Accordingly, the valve increase means for preventing such unrestricted fluid flow to the drainage location in the event of a sudden increase in the differential pressure.

The internal construction and operation of the three stage valve may best be understood by reference to FIGS. 2-6. As illustrated, the valve includes a disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or a similar material bonded together over the inner housing. The dimensions of the inner and outer housings are selected so as to be compatible with subcutaneous implantation of the valve over the cranium 29 (FIG. 1).

Figure 4:
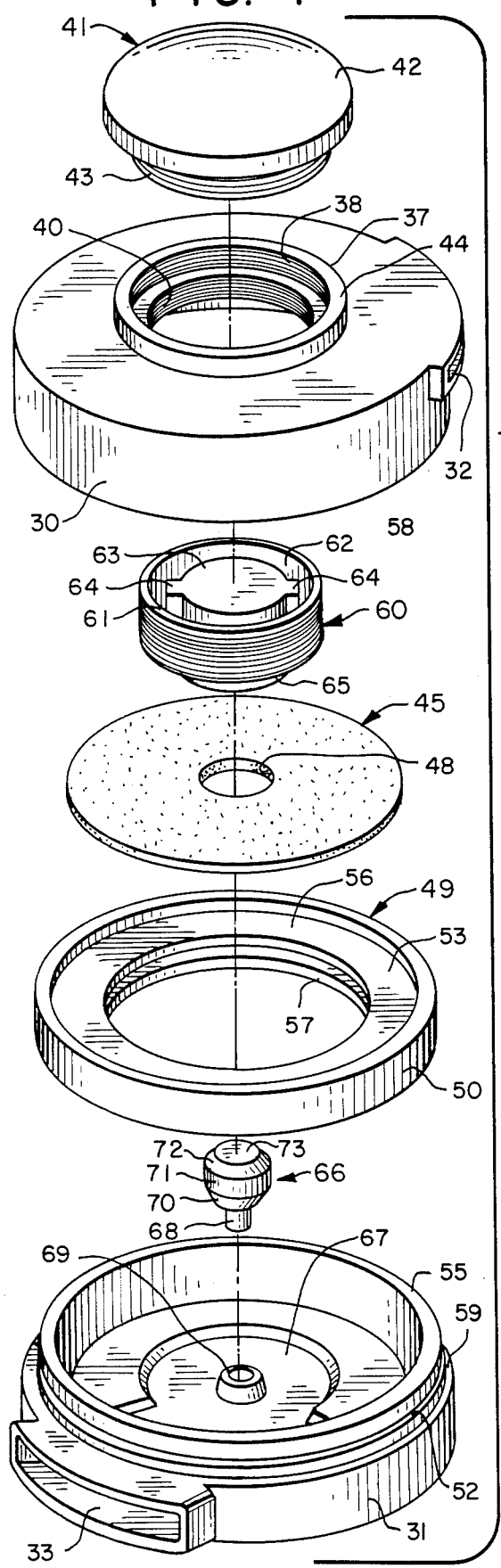
FIG. 4 is an exploded perspective view of the pressure regulator valve showing the specially constructed and combined members of the valving mechanism as well as other principal elements of the valve.
Figure 5:
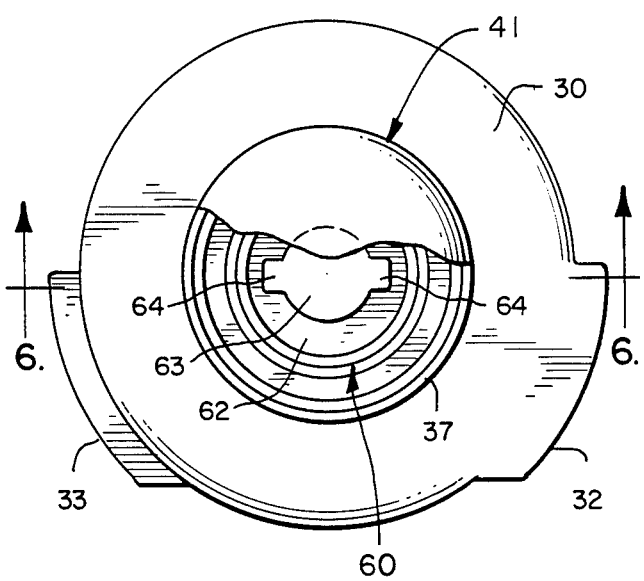
FIG. 5 is a top plan view, partially in section, of the three stage pressure regulator valve shown in FIG. 4.

As is best illustrated in FIGS. 3 and 4, the inner housing 26 comprises two circular cup-shaped housing member 30 and 31. Housing member 30 includes an inlet port 32, and housing member 31 includes an outlet port 33, by means of which fluid can pass to or from the interior region of the housing. In this regard, outer housing members 27 and 28 are provided with internal conduits 35 and 36, which provide fluid communication between inlet port 32, outlet port 33 and housing 26, respectively.

Upper housing member 30 is provided with an aperture 37 through the upper surface thereof. As illustrated in FIG. 4, the aperture 37 includes a region 38 of relatively larger diameter coaxially aligned above a region of relatively smaller diameter 40. Both the relatively larger diameter and smaller diameter regions of the aperture are internally threaded as illustrated in order to seal the aperture while still allowing ready access to the interior region of the housing, the upper housing member 30 includes a removable cap 41 having a domed upper surface 42 and an externally threaded cylindrical lower portion 43 dimensioned to engage the threads of region 38 of aperture 37. To provide a tight seal between the cap and the housing, the upper housing member may include a raised annular seat 44 adjacent the periphery of the aperture against which the cap bears as it is turned into the upper housing member.

Referring to FIGS. 4 and 6 in particular, pressure relief valve 12 includes partition means in the form of a diaphragm 45 which extends laterally across the interior region of the housing to divide that region into first and second interior chambers 46 and 47 (FIG. 6), respectively. The diaphragm 45 may be fashioned from a flexible biocompatible material, such as silicone rubber and, as illustrated, is of uniform thickness and provided with a fluid flow orifice 48 centrally thereof. The diaphragm 45 is basically disc-shaped and clamped in the valve housing along its outer periphery while extending flexibly across the interior of the housing to place the fluid flow orifice 48 essentially centrally of the housing. The free portion of the diaphragm 45 within the housing presents sufficient exposed surface area to be responsive to pressure applied thereto and thereby being movable within the housing in response to differential pressure as might result from a difference in pressure in the first and second interior chambers 46 and 47, respectively.

An annular diaphragm mounting ring 49 is received between the upper and lower housing members 30 and 31. The ring 49 includes a vertically extending outer rib 50 which, as best shown in FIG. 6, is cooperatively clamped by the surface portions of opposing grooves 51 in the upper housing member 30 and 52 in the lower housing member 31. The diaphragm mounting member 49 includes an annular web portion 53 located just inwardly of the outer vertical rib 50 and formed integrally therewith. The web portion 53 is clamped between opposing shoulder-like surfaces 54 of the upper housing member 30 and 55 of the lower housing member 31. Interiorly of the housing extending into chambers 46 and 47, the diaphragm mounting member 49 includes a bifurcated inner and annular diaphragm clamping area defined by an upper clamping portion 56 and a lower clamping portion 57. The outer annular edge of the diaphragm 45 is suitable clamped between these portions 56 and 57 so as to be operatively retained within the valve housing. The diaphragm mounting member 49 including the vertical rib portion 50 an the web portion 53 assists in sealing the upper housing member 30 relative to the lower housing member 31. To complete this sealing action, the upper housing member 30 is provided with an outer depending sleeve portion 58 which is circumferentially continuous and which tightly engages a step portion 59 formed in the lower housing member 31 and being circumferentially continuous thereon.

Referring in particular to FIGS. 4 and 6, the upper housing member 30 has received therein a valve closure member 60 which is of one piece configuration and is of cylindrical shape. The closure member 60 includes an outer upstanding sleeve 61 which is externally threaded and which is advancedly and retractably received in the smaller diameter 40 and the threads thereof forming a part of the aperture 37 of the upper housing member 30. Inwardly of the sleeve 61 is formed an annular groove 62 which surrounds a centrally raised boss 63 provided with integral outwardly projecting and oppositely aligned ribs 64. The removable cap 41 covers the valve closure member 60 but, as can readily be appreciated, can be removed to permit access to the closure member. In this manner a suitable tool may be inserted in the groove 62 of the valve closure member 60 to engage the ribs 64 to adjust the position of the valve closure member 60 relative to the diaphragm.

The bottom surface of the valve closure member 60 is provided with a downwardly projecting annular valve closure rib 65 which, as best illustrated in FIG. 6, is of generally V-shaped configuration projecting downwardly to engage the diaphragm 45 annularly and outwardly of the fluid flow orifice 48. The inherent degree of resistance to flexure of the diaphragm 45, or memory if preferred, is sufficient to establish closing engagement between the diaphragm and closure rib 65 to occlude the orifice 48 and prevent fluid flow in the valve in the absence of an operative differential pressure.

The assembly is completed with the provision of a fluid flow control member or restrictor 66 which is mounted in the bottom wall 67 of the lower housing member 31 and which projects upwardly into the second chamber 47 in alignment with the fluid flow orifice 48 of the diaphragm 45. The fluid flow restrictor or pin 66 includes a base stem 68 which is fixedly received in an upwardly projecting boss 69 integrally formed in the bottom wall 67 of the lower housing member 31. The operative portion of the restrictor pin 66 projecting above the mounting boss 69 includes, in an upwardly direction, a diverging frusto-conical surface 70 merging with a vertically extending cylindrical surface 71 which, in turn, merges upwardly with a converging frusto-conical surface portion 72 which in turn terminates in a flat top surface 73. Thus, the fluid flow control member 66 can be described as including a centrally located cylindrical face portion positioned between a pair of diverging face portions, such portions cooperative with the flexible valve seat which defines the fluid flow orifice 48 to control fluid flow control from the interior chamber 46 to the interior chamber 47.

When no differential pressure acts on diaphragm 45, the central annular portion of the diaphragm 45 surrounding the fluid flow orifice 48 is in engagement with the valve closure rib 65 as shown in FIG. 6 so that the orifice 48 is totally occluded to prevent the passage of CSF between the first and second chambers. Downward travel of the diaphragm progressively opens the orifice, eventually resulting in the introduction of the fluid flow control member 66 and the partial occlusion of the passage between the first and second chambers. The dimension of the fluid flow control member 66 is selected so that it will barely pass through the orifice at its widest point which is that portion defining the vertical cylindrical surface 71. By way of example, in one embodiment of the valve, clearance between these elements was on the order of 0.001 of an inch.

Figure 10:
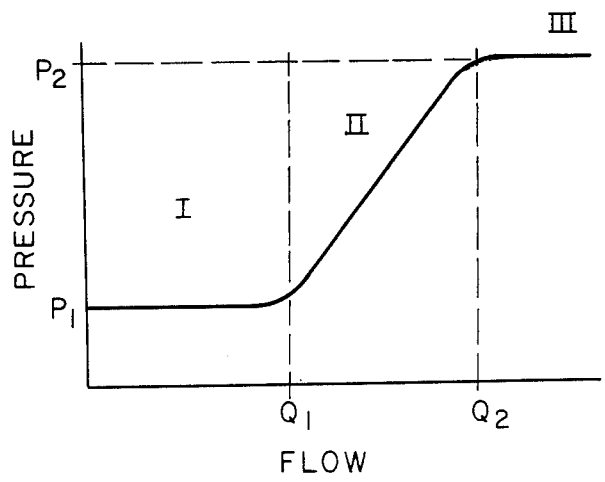
FIG. 10 is a graphical depiction of certain pressure and flow characteristics of the three stage pressure relief valve useful in understanding the operation thereof.

The operation of the valve is illustrated in FIGS. 6-10. FIG. 6 illustrates the operation of the valve in the absence of applied CSF pressures. FIGS. 7-9 illustrate the operation of the valve in response to various levels of CSF pressures. FIG. 10 is a graphical depiction of pressure vs. flow characteristics of the valve.

Basically, the pressure relief valve 12 normally operates to maintain a predetermined differential pressure $P_1$ between fluids in the brain ventricle and at the selected discharge location of the body. The valve accomplishes this by adjusting the fluid flow rate Q so that the pressure $P_1$ is maintained. This operation of the valve is shown in region I of FIG. 10.

When differential pressure rapidly increases, such as when the patient stands, a flow rate greater than a preselected rate $Q_1$ is necessary to maintain pressure $P_1$. However, such a flow rate may create the risk of undesirable hyperdrainage of the brain ventricle. Accordingly, when a rapid increase in differential pressure occurs, the valve automatically serves to maintain a relatively constant desired rate of fluid flow despite changes in differential pressure, as depicted in region II of FIG. 10. In a practical valve, the flow rate will not be entirely independent of the applied differential pressure but rather will increase from a lower flow rate $Q_1$ to a higher flow rate $Q_2$ as differential pressure increases between first pressure $P_1$ and a second pressure $P_2$, as indicated by the solid line in FIG. 10. Flow rates $Q_1$ and $Q_2$ are sufficiently low so that during a temporary rapid increase in differential pressure, pressure will return to normal before a quantity of CSF sufficient to cause adverse side effects may flow through the valve. In a typical valve, $Q_1$ and $Q_2$ might be 0.4 ml./min. and 0.8 ml./min., respectively, while first and second pressures $P_1$ and $P_2$, may have values of 80 and 350 millimeters of water, respectively.

While it is desirable to avoid high flow rates through the valve in order to avoid hyperdrainage of the ventricle, it may, under certain emergency conditions, be desirable to allow rapid shunting of CSF in order to avoid possible brain damage. When the valve is operating in region II, increases in differential pressure tend to close the valve between the first and second interior chambers. To avoid the possibility of building extremely high ventricular CSF pressure, the valve is constructed so that when differential pressure exceeds a predetermined pressure $P_2$ substantially higher than pressure $P_1$, the valve once again operates to allow a fluid flow rate sufficient to maintain a differential pressure no higher than pressure $P_2$. This operation is depicted in region III of FIG. 10. When the valve is operating in this region, further increases in differential pressure result in an increase in fluid flow through the valve thereby stabilizing differential pressure.

FIGS. 6–9 illustrate the operation of the valve in the regions previously described. CSF applied to the inlet port 21 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts an upwardly directed force on the lower surface of the diaphragm. Accordingly, any differential pressure between CSF in the brain ventricle and fluid at the drainage location results in vertical deflection of the diaphragm.

As shown in FIG. 6, when differential pressure is negative or non-existent, the annular portion of the diaphragm 45 surrounding the fluid flow orifice 48 contacts the closure rib 65 of the closure member 60 and the orifice 48 is totally occluded, thereby preventing CSF flow between chambers 46 and 47.

When the differential pressure is relatively low, such as when the valve is operating in region I of FIG. 10, the resulting slight downward movement of the diaphragm is sufficient to displace the same relative to the closure rib 65 as shown in FIG. 7, thereby allowing CSF to pass through orifice 48 from chamber 46 to chamber 47. As shown, the downward deflection of the diaphragm is sufficient to allow the passage of CSF through the orifice, yet the enlarged cylindrical surface 71 of the restrictor pin 66 is sufficiently removed from the orifice so as not to interfere with the flow of CSF between the chambers. Thus, the valve acts primarily as a constant pressure device whereby the pressure differential $P_1$ is maintained between the CSF in chambers 46 and 47. An increase in differential pressure results in a downward deflection of the diaphragm, thereby further opening the valve to allow greater CSF flow between the chambers. Similarly, a decrease in pressure allows the diaphragm to move toward the closure rib restricting flow between the chambers and causing pressure in chamber 46 to increase. It will be noted that the regulated pressure $P_1$ in this mode can be adjusted by rotating the valve closure member 60 to vary the vertical position of the closure rib 65 relative to the diaphragm 45.

FIG. 8 illustrates the operation of the valve when a sudden increase in differential pressure is applied to the valve. When such an event occurs, the pressure differential exceeds the predetermined regulated pressure $P_1$ and the valve operates in region II of FIG. 10. The downward displacement of the diaphragm 45 is now sufficient to cause the orifice 48 to receive the enlarged cylindrical surface portion 71 of the restrictor pin 68 causing partial occlusion of the orifice 48. As the diaphragm 45 stretches, at least in its central area, the response to increased differential pressure, the orifice 48 increases somewhat in size thus cooperating with the location and size of the fluid flow control member 66 to permit more controlled and extensive response to variations in differential pressure in a smaller area. This is of significance in connection with the need of miniaturization of a valve of this type. Thus, the cooperative action of the flexible and variable orifice 48 and the configuration of the restrictor pin 66 results in a further occlusion of the orifice 48. This additional occlusion occurring by reason of increasing differential pressure is sufficient to offset the higher flow rate ordinarily resulting from increased pressure, thus providing a relatively uniform rate of fluid flow between the chambers despite such an increase in differential pressure. Accordingly, in this condition, the valve acts primarily as a constant flow device permitting the passage of fluid from chamber 46 to chamber 47 at a relatively constant predetermined rate despite changes in applied differential pressure.

FIG. 9 illustrates operation of the valve in region III of FIG. 10, such as would occur when the differential pressure exceeds a predetermined pressure level $P_2$. In this condition, differential pressure displaced the diaphragm to a degree sufficient to cause the restrictor pin 66 to extend past the orifice 48. The orifice is now less restricted than in region II wherein the vertical cylindrical surface portion 71 is received within the orifice 48 of the diaphragm 45. When the valve is operating in this manner, increases in differential pressure cause the diaphragm in the area of the orifice to be further displaced away from the restrictor, thereby further opening the orifice and allowing a greater fluid flow rate. Thus, the valve operates essentially as a constant pressure device whereby differential pressure greater than the predetermined maximum pressure $P_2$ is prevented.

The provision of the flexible valve seat in conjunction with an expandable and retractable orifice provides a number of advantages. As mentioned above, a more controlled response to changes in differential pressure can be accomplished in a smaller area thus greatly assisting in miniaturization of the valve. The cost of a separate rigid seat and the assembly of such a seat to a flexible diaphragm is eliminated. The diaphragm, and particularly the area of the same which surrounds and defines the flexible seat, can be varied in thickness, resiliency or in other aspects to accommodate variable treatment needs, such as different predetermined pressures $P_1$ and $P_2$. An adjustable mold can be used to form various diaphragms which exhibit different functional characteristics.

The fluid flow control member 66 may be advantageously formed as a single piece member from a hard biocompatible material such as ruby, sapphire or the like. Because of the non-complex surface portions of this member, such surfaces can be accurately formed by economical, well known lathe machining operations. The flexible and expandable nature of the diaphragm valve seat in conjunction with the stationary restrictor pin 66 tends to remove foreign materials which may tend to clog the valve.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A valve for regulating the flow of fluid from one location in the body to another location, comprising:
   a bio-compatible housing;
   a flexible one-piece bio-compatible diaphragm dividing the interior of said housing into first and second interior chambers, said diaphragm including an integral valve seat portion defining a fluid passageway opening from said first interior chamber to said second interior chamber, and defining a first valving surface concentrically oriented with respect to the axis of said fluid passageway, said valve seat portion having a static position within said housing in the absence of a pressure differential between said chambers;
   inlet port means for establishing fluid communication between said first interior chamber and the one location;
   outlet port means for establishing fluid communication between said second interior chamber and the other location;
   means comprising an elongated bio-compatible valve stem member attached at one end to said housing primarily within said second chamber and extending therefrom along the axis of said fluid passageway toward said first chamber, said valve stem member defining a plurality of additional valving surfaces for coacting with said first valving surface to form a flow restriction within said passageway between said first and second chambers;
   said additional valving surfaces including, progressing from said first chamber toward said second chamber, a first surface of generally relatively lesser radial extent from said axis for providing a relatively lesser flow restriction in said passageway, a second surface of generally relatively greater radial extent for providing a relatively greater flow restriction in said passageway and a third surface of generally lesser radial extent similar to said first surface to provide a relatively lesser flow restriction in said passageway;
   valve closure means coacting with said valve seat portion in said static position to close said passageway to provide a first valving mode wherein flow between said first and second interior chambers is prevented; and
   said valve seat portion being displaceable from said static position in a direction along said axis of said fluid passageway away from said valve closure member in response to an increase in pressure differential between said first interior chamber and said second interior chamber to cause said first valving surface to successively coact with said first, second and third surfaces of said valve stem member thereby providing second, third and fourth valving modes, in said second valving mode fluid flow occurring between said interior chambers so as to maintain a first substantially constant predetermined pressure in said first chamber, in said third valving mode fluid flow remaining substantially constant between said chambers notwithstanding changes in differential pressure, and in said fourth valving mode fluid flow occurring between said chambers to maintain a second substantially constant predetermined pressure in said first interior chamber.

2. A flow regulating valve as defined in claim 1 wherein said first valving surface is formed from flexible and stretchable material and is inherently biased into engagement with said valve closure member when said valve seat is in said static position to provide a predetermined threshold pressure differential at which flow occurs between said first and second interior chambers.

3. A flow regulating valve as defined in claim 1 wherein said first surface of said valve stem member is generally frusto-conical and of progressively increasing diameter, said second surface of said valve stem member is generally cylindrical and vertically extending, and said third surface of said valve stem member is generally frusto-conical and of progressively decreasing diameter.

4. A flow regulating valve as defined in claim 2 wherein said valve closure member includes an annular rib of V configuration arranged to engage said valve seat portion to prevent fluid flow between said first and second interior chambers in said static position of said valve seat portion.

5. A flow regulating valve as defined in claim 4 wherein said first surface of said valve stem member is generally frusto-conical and of progressively increasing diameter.

6. A flow regulating valve as defined in claim 1 wherein said diaphragm and valve seat portion thereof are formed from flexible and stretchable material to permit movement thereof in response to pressure differential, said first valving surface being expandable and retractable in response to such movement, said first valving surface and said valve stem member being dimensioned relative to one another so that the greatest radial dimension of said valve stem member will barely be received and through said fluid passageway.

7. A flow regulating valve as defined in claim 3 wherein said diaphragm and valve seat portion thereof are formed from flexible and stretchable material to permit movement thereof in response to pressure differential, said first valving surface being expandable and retractable in response to such movement, said first valving surface and said valve stem member being dimensioned relative to one another so that the greatest radial dimension of said valve stem member will barely be received in and through said fluid passageway.

* * * * *